United States Patent
Roberts et al.

(10) Patent No.: US 6,436,704 B1
(45) Date of Patent: Aug. 20, 2002

(54) HUMAN PANCREATIC EPITHELIAL PROGENITOR CELLS AND METHODS OF ISOLATION AND USE THEREOF

(75) Inventors: Penelope E. Roberts; Jennie Powell Mather, both of Millbrae, CA (US)

(73) Assignee: Raven Biotechnologies, Inc., South San Francisco, CA (US)

(*) Notice: Subject to any disclaimer, the term of this patent is extended or adjusted under 35 U.S.C. 154(b) by 0 days.

(21) Appl. No.: 09/546,577

(22) Filed: Apr. 10, 2000

(51) Int. Cl.$^7$ ............................. C12N 5/00; C12N 5/02; C12N 5/06; C12N 5/08

(52) U.S. Cl. ................. 435/366; 435/325; 435/363; 435/378; 435/383; 435/405

(58) Field of Search ............................. 424/93.7, 93.1; 435/325, 378, 1.1, 363, 405, 383; 800/8; 514/44

(56) References Cited

U.S. PATENT DOCUMENTS

| | | | |
|---|---|---|---|
| 5,587,309 A | | 12/1996 | Rubin et al. |
| 5,834,308 A | | 11/1998 | Peck et al. |
| 5,888,705 A | | 3/1999 | Rubin et al. |
| 6,001,647 A | * | 12/1999 | Peck et al. ............ 435/325 |
| 6,004,528 A | | 12/1999 | Bergstein |

FOREIGN PATENT DOCUMENTS

| | | | |
|---|---|---|---|
| EP | 0 363 125 A | * 4/1990 | ............ C12N/5/00 |
| WO | WO 95/29988 A1 | 11/1995 | |
| WO | WO 97/15310 | 5/1997 | |
| WO | WO 00/47720 A2 | 8/2000 | |
| WO | WO 01/42789 A1 | 6/2001 | |

OTHER PUBLICATIONS

Beattie, G.M. et al., (1994) "Acid β–galactosidase: a developmentally regulated marker of endocrine cell precursors in the human fetal pancreas" *Journal of Clinical Endocrinology and Methabolism* 78(5):1232–1240.

Hua, Y. and Zhao–Guang, W. (1989) "Morphological and functional studies on microencapsulated human fetal pancreatic tissue" *Chinese Medical Journal* 102(10):786–790.

Hunziker, E. and Stein, M. (2000) "Nestin–expressing cells in the pancreatic islets of langerhans" *Biochemical and Biophysical Research Communications* 271:116–119.

Kritzik, M.R. et al., (1999) "PDX–1 and Msx–2 expression in the regenerating and developing pancreas" *Journal of Endocrinology* 163:523–530.

Kritzik, M.R. et al., (2000) "Expression of ErbB receptors during prancreatic islet development and regrowth" *Journal of Endocrinology* 165:67–77.

Miettinen, P.J. et al., (1993) "Insulin–like growth factor–II and transforming growth factor–α in developing human fetal pancreatic islets" *Journal of Endocrinology* 138:127–136.

Stephan, Jean–Philippe et al., (Dec. 1997). "Characterization of Cell Surface Proteins Using Antibodies Raised to Antigens From Pancreatic Cell Lines," Abstract 1905–presentation materials:17 pages.

(List continued on next page.)

Primary Examiner—Deborah Crouch
Assistant Examiner—Joseph T. Woitach
(74) Attorney, Agent, or Firm—Morrison & Foerster LLP

(57) ABSTRACT

The invention discloses a substantially pure population of human pancreatic progenitor cells and methods of isolating and culturing the pancreatic progenitor cells. By carefully manipulating the microenvironment of the pancreatic progenitor cells, multiple passages are attainable wherein the pancreatic progenitor cells do not senesce and furthermore, are capable of becoming functional exocrine or endocrine cells. In addition, several methods of use of human pancreatic progenitor cells are disclosed herein.

13 Claims, 8 Drawing Sheets

(7 of 8 Drawing Sheet(s) Filed in Color)

OTHER PUBLICATIONS

Barnes et al., (1980). "Methods for growth of cultured cells in serum–free medium" *Anal. Biochem.* 102:255–270.

Buck et al., (1982). "Monoclonal antibodies specific for cell culture mycoplasmas" In Vitro 18(4):377–381.

Freshney, R.I., (ed), (1987). *Animal Cell Culture* pp.vii–xii. (Table of Contents).

Ganong, William F., (1991). "Regulation of gastrointestinal function" in *Review of Medical Physiology*, fifteenth edition, Appleton and Lange, (eds), Chapter 26, pp. 448–447.

Ham et al., (1979). "Media and growth requirements" *Meth. Enzy.* 58:44–93.

Harlow and Lane, (eds), (1988). *Antibodies, A Laboratory Manual* pp. iii–ix. (Table of Contents).

Köhler et al., (1975). "Continuous cultures of fused cells secreting antibody of predefined specificity" *Nature* 256:495–497.

Mather, Jennie P. and Roberts, Penelope E., (1998). *Introduction to Cell and Tissue Culture* Plenum Press, New York pp. xi–xiv. (Table of Contents).

Olumi et al., (1999). "Carcinoma–associated fibroblasts direct tumor progression of initiated human prostatic epithelium" *Cancer Research* 59:5002–5011.

Stephan et al., (1999)."Selective cloning of cell surface proteins involved in organ development: Epithelial glycoprotein is involved in normal epithelial differentiation" *Endocrinology* 140:5841–5854.

Levine et al. Transplantation Proceedings 27(6):3410, Dec. 1995.*

Mathers et al. Experientia 41(1):116–8, Jan. 1985.*

Kolar et al. Pancreas 15(3):265–71, Oct. 1997.*

Levine et al. Cell Transplantation 3(4):307–13, Jul. 1994.*

Dabeva et al. Proceedings of the National Academy of Science 94:7356–61, Jul. 1997.*

Mandel, T.E. Journal of Molecular Medicine 77:155–160, Jan. 1999.*

Taniguchi et al. Journal of Surgical Research 70:41–45, 1997.*

* cited by examiner

HUMAN PANCREATIC EPITHELIAL PROGENITOR CELLS AND METHODS OF ISOLATION AND USE THEREOF

TECHNICAL FIELD

This invention is in the field of developmental biology and cell biology. Specifically, this invention relates to a population of pancreatic epithelial progenitor cells that are capable of differentiating into functional endocrine and exocrine cells, methods of isolating the pancreatic epithelial progenitor cells, characterization of pancreatic epithelial progenitor cells, and uses of the pancreatic epithelial progenitor cells.

BACKGROUND ART

Stem cell and progenitor cell isolation and characterization are the subjects of intense research because of the great potential of such cells. The totipotent stem cells, which have the capacity to become any type of cell in a human body, give rise to progenitor cells more differentiated than the totipotent cell. One of these types of progenitor cells is the predetermined pancreatic epithelial progenitor cell. The pancreatic epithelial progenitor cells have the ability to become different types of pancreatic epithelial cells. The different types of pancreatic epithelial cells include acinar cells, islet cells, and ductal cells. Acinar cells are generally found near the head of the pancreas and contain zymogen granules which are readily visible by electron microscopy. Acinar cells perform exocrine functions by discharging alkaline digestive juices into the small intestine. Approximately 1500 mL of pancreatic juices are secreted per day and include enzymes needed to break up lipids and proteins. Ganong, William F. Review of Medical Physiology, Chapter 26 "Regulation of Gastrointestinal Function", Fifteenth Edition, Appleton and Lange (1991). There are four types of islet cells, also known as islets of Langerhans, islet-$\alpha$, islet-$\beta$, islet-$\delta$, and islet-PP. Islet-$\alpha$ cells secrete glucagon which promotes gluconeogenesis, i.e. breakdown of energy reserves to generate more circulating glucose. Islet-$\beta$ cells secrete insulin which promotes storage of circulating glucose into accessible energy resources. In type I diabetes mellitus, otherwise known as juvenile diabetes, it is thought that autoimmune attacks on islet-$\beta$ cells cause defective islet-$\beta$ cell function, thereby causing a lack of insulin to reduce the levels of circulating glucose. Islet-$\delta$ cells secrete somatostatin which regulates the secretion of glucagon and insulin. The fourth islet cell type islet-PP (pancreatic polypeptide) does not yet have a known function within the pancreas. Another type of sub-pancreatic cell is the ductal cell. These cells line the ducts that connect different parts of the pancreas.

Isolation of pancreatic epithelial progenitor cells, as with other types of progenitor cells, is difficult because of the ephemeral nature of progenitor cells. Manipulation of progenitor cells required for isolation may disturb the fragile progenitor status of these cells and may cause them to differentiate. Contact with growth factors or substrates may also induce a pancreatic progenitor cell to begin differentiating into exocrine or endocrine cells. Research in the area of pancreatic cells has resulted in the establishment of several pancreatic epithelial cell lines derived from rats. Stephan, J. et. al. Endocrinology 140:5841–5854, (1999). Other research includes the isolation of human adult pancreatic cells and the induction of these pancreatic cells to proliferate into islet-$\beta$-like structures with hepatocyte growth factor/scatter factor (HGF/SF). Jeffrey et. al. U.S. Pat. No. 5,888,705. Other research work involves inducing growth of islet cells from adult pancreatic cells by culturing first in serum-containing, low-glucose medium and then switching to medium with higher serum and glucose content. WO 9715310. Still other research in the area of pancreatic progenitor cells includes isolating progenitor cells from pre-diabetic adults and culturing in a serum-containing, pre-defined media that promotes the growth of functional islet cells. U.S. Pat. No. 5,834,308. However, all of these "progenitor" cells give rise only to islet cells. Pancreatic cells of the aforementioned research do not have the capacity to differentiate into both endocrine and exocrine cell types. It seems likely that the pancreatic cells of the aforementioned research are further committed down the differentiation pathway of pancreatic progenitor cells and therefore are different types of pancreatic cells than the human pancreatic progenitor cells of this invention. Furthermore, culturing conditions used in the aforementioned research wherein serum is used to supplement media may have adverse consequences. Serum, the fluid portion of blood after blood has been allowed to clot, contains many biomolecules such as albumin and $\alpha$, $\beta$, -globulins. In vivo, cells are not normally exposed to an equivalent of serum unless tissue injury was involved. Therefore, culturing pancreatic cells in serum may not accurately reflect the physiological parameters within which pancreatic cells exist in vivo.

The ideal population of pancreatic progenitor cells should be able to differentiate into exocrine (i.e. acinar) cells, endocrine (i.e. islet-$\alpha$, islet-$\beta$, islet-$\delta$, and islet-PP) cells as well as ductal cells. Such a population of pancreatic progenitor cells may be useful in clinical settings, for example to treat certain types of diabetes or to treat functionally defective pancreatic cells by transplantation of pancreatic progenitor cells that can differentiate into functional pancreatic cells. Accordingly, there is a need for a population of pancreatic progenitor cells and methods of isolating and culturing the pancreatic progenitor cells such that the differentiation potential of the pancreatic progenitor cells is retained while permitting proliferation and avoiding senescence of these cells. The pancreatic progenitor cells and methods of isolating and culturing these pancreatic progenitor cells disclosed herein satisfies these needs and also provides related advantages.

DISCLOSURE OF THE INVENTION

This invention is related to the field of developmental and cell biology. In one aspect, the invention relates to a population of substantially pure human pancreatic epithelial progenitor cells which have a pluripotent capability to differentiate into functional exocrine or endocrine pancreatic cells.

In another aspect of this invention, the invention relates to methods of isolating a population of substantially pure human pancreatic epithelial progenitor cells which have the pluripotent capability to differentiate into functional exocrine or endocrine pancreatic cells.

In yet another aspect of this invention, the invention relates to methods of maintaining a population of substantially pure human pancreatic epithelial progenitor cells which have the pluripotent capability to differentiate into functional exocrine or endocrine pancreatic epithelial cells and maintaining or culturing these pancreatic progenitor cells such that the cells retain their pluripotent capacity while avoiding senescence.

In still another aspect of this invention, the invention relates to methods of providing a source of immunogen and the uses of a substantially pure population of pancreatic progenitor cells as an immunogen.

In still another aspect of this invention, the invention relates to methods of generating a human pancreatic tissue model using a substantially pure population of pancreatic progenitor cells as a source of pancreatic cells and introducing the pancreatic progenitor cells into a non-human, mammalian recipient.

In another aspect of this invention, the invention relates to methods of providing cell therapy whereby a substantially pure population of human pancreatic progenitor cells are introduced into a recipient.

In another aspect of this invention, the invention relates to methods of providing pharmaceutical drug development wherein a substantially pure population of human pancreatic progenitor cells are used as a source of pancreatic biological components in which one or more of these pancreatic biological components are the targets of the drugs that are being developed.

In another aspect of this invention, the invention relates to methods of providing bioassay development wherein a substantially pure population of human pancreatic progenitor cells are used as a source of nucleic acids or proteins and wherein these nucleic acids or proteins are used as one or more principal components in a bioassay or the development of a bioassay.

BRIEF DESCRIPTION OF THE DRAWINGS

This patent or application file contains at least one drawing executed in color. Copies of this patent or patent application with color drawing(s) will be provided by the U.S. Patent and Trademark Office upon request and payment of the necessary fee.

FIG. 1A (left) shows pancreatic epithelial cells grown in CMRL 1066 medium with fibronectin coating on the plate. The large, rounded cells are pancreatic epithelial cells. FIG. 1B (right) shows pancreatic epithelial cells grown in F 12/DMEM medium. The pancreatic epithelial cells have flatten out to form a monolayer.

FIG. 3A shows islet formation in the tissue recombinant graft at a magnification of 20x. FIG. 3B shows islet formation in the tissue recombinant graft at a magnification of 60x. FIG. 3C shows formation of islet, duct, and acinar tissue within the tissue recombinant graft. FIG. 3D shows ductal formation in the tissue recombinant graft. FIG. 3E shows formation of clusters (or aggregates) of acinar cells in the tissue recombinant graft.

MODES FOR CARRYING OUT THE INVENTION

Figure 1:
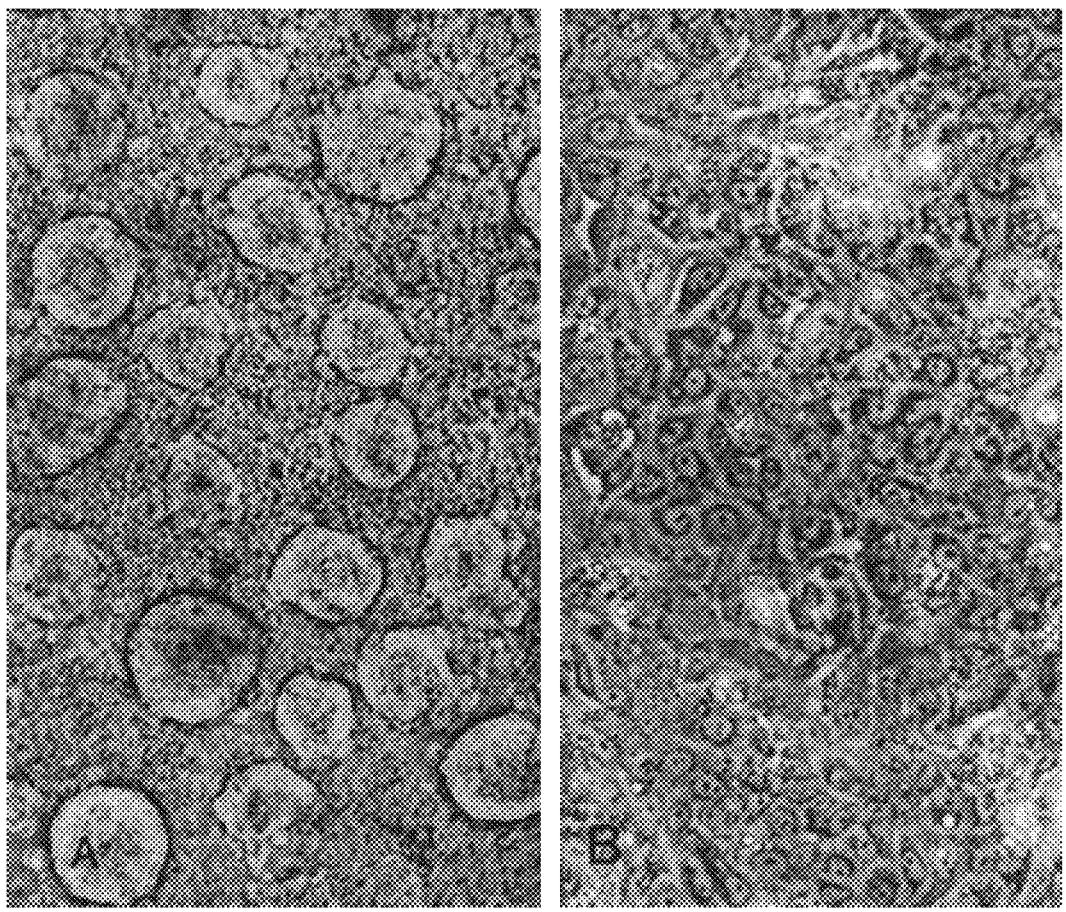
FIG. 1 shows human pancreatic ductal epithelial cells grown in two different types of media.

The following detailed description of the invention is provided to aid those skilled in the art in practicing the present invention. This detailed description should not be construed to limit the present invention, as modifications of the embodiments disclosed herein may be made by those of ordinary skill in the art without departing from the spirit and scope of the present invention. Throughout this disclosure, various publications, patents, and published patent specifications are referenced by citation. The disclosure of these publications, patents, and published patents are hereby incorporated by reference in their entirety into the present disclosure.

The practice of the present invention will employ, unless otherwise indicated, conventional techniques of immunology, molecular biology, microbiology, cell biology and recombinant DNA, which are within the skill of the art. See, e.g., Sambrook, et al. MOLECULAR CLONING: A LABORATORY MANUAL, $2^{nd}$ edition (1989); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)).

Definitions

As used in the specification and claims, the singular form "a", "an" and "the" include plural references unless the context clearly dictates otherwise. For example, the term "a cell" includes a plurality of cells, including mixtures thereof.

As used in the specification and claims, the terms "pancreatic epithelial progenitor cells" and "pancreatic progenitor cells" are interchangeable and refer to "pancreatic epithelial progenitor cells" and "pancreatic progenitor cells" of human origin.

"Pancreatic epithelial progenitor cells" and "pancreatic progenitor cells" refer to dividing progenitor cells found in the pancreas that have not yet committed to an essentially non-dividing stage of end differentiation. "Pancreatic epithelial progenitor cells" and "pancreatic progenitor cells" are derived ultimately from totipotent cells that give rise to pluripotent, tissue-specific cells. These pluripotent, tissue-specific, dividing progenitor cells can give rise to cells of the endoderm, ectoderm, or mesoderm. Of the endodermal multipotent cells, some differentiate into gut-specific, dividing progenitor cells. Of the gut-specific progenitor cells, some are pre-determined to become pancreatic cells. It is at this stage of development that the population of cells claimed herein resides. More specifically, the population of "pancreatic epithelial progenitor cells" and "pancreatic progenitor cells" disclosed herein is between the stage at which a gut-specific progenitor cell is pre-determined to become a pancreas (or part of a pancreas) and the stage at which a pancreas-specific progenitor cell is committed to becoming a sub-pancreatic type of cell. Pancreas-specific progenitor cells can differentiate into several types of cells: acinar, ductal, and islet-α, islet-β, islet-δ, and islet-PP. One exocrine function of the acinar cells is the secretion of digestive juices into the intestine. One endocrine function of the islet cells is the secretion of glucagon (islet-α) and insulin (islet-β). The pancreatic progenitor cells of this invention have not differentiated into any of the aforementioned types of sub-pancreatic cells but have the capacity to become any of these cells.

"Sub-pancreatic" refers to cellular infrastructure within the pancreas as a whole organ. Examples of sub-pancreatic cells include, but are not limited to, acinar, ductal, and islet cells.

"Totipotent cell" and "totipotent stem cell" are used interchangeably throughout and refer to a stem cell that has the capacity to become any type of cell in a mammalian body.

"Pluripotent" and "multipotent" are used interchangeably throughout and refer to a stage where a cell can still become one of a plurality of cells but can no longer become any type of cell in the body. "Pluripotent" cells are not referred to as "stem cells" but rather "progenitor cells" because they are progenitors to one or more type of a plurality of cells.

As used herein, "pre-determined pancreatic" refers to a stage of development of a multipotent cell that is beyond the stage of being gut-specific and before the stage of terminally differentiated pancreatic cells (such as acinar, islet, or ductal cells). Cells which are "pre-determined pancreatic" are committed to becoming pancreatic cells but have not begun to develop into terminally differentiated pancreatic cells yet. Different factors cause pre-determined pancreatic cells to begin differentiating. Non-limiting examples include exposure to serum, exposure to insulin growth factor (IGF) or epidermal growth factor (EGF), contact with surrounding tissue, microenvironment of the cells, and cell-cell contact with surrounding tissue. The chain of development begins with a totipotent stem cell which can become any cell in the body. The totipotent stem cell is a true stem cell because of its cellular omnipotency. At any stage beyond the totipotent stem cell, cells become a "pre-determined progenitor" because they have been committed down a pathway that no longer enables the cell to become any kind of cell in the body.

An "antibody" is an immunoglobulin molecule capable of binding an antigen. As used herein, the term encompasses not only intact immunoglobulin molecules, but also anti-idiotypic antibodies, mutants, fragments, fusion proteins, humanized proteins and modifications of the immunoglobulin molecule that comprise an antigen recognition site of the required specificity.

The term "antigen" is a molecule which can include one or more epitopes to which an antibody may bind. An antigen is a substance which can have immunogenic properties, i.e., induce an immune response. Antigens are considered to be a type of immunogen. As used herein, the term "antigen" is intended to mean fill length proteins as well as peptide fragments thereof containing or comprising one or a plurality of epitopes.

The terms "surface antigens" and "cell surface antigen" are used interchangeably herein and refer to the plasma membrane components of a cell. These component include, but are not limited to, integral and peripheral membrane proteins, glycoproteins, polysaccharides, lipids, and glycosylphosphatidylinositol (GPI)-linked proteins. An "integral membrane protein" is a transmembrane protein that extends across the lipid bilayer of the plasma membrane of a cell. A typical integral membrane protein consists of at least one membrane spanning segment that generally comprises hydrophobic amino acid residues. Peripheral membrane proteins do not extend into the hydrophobic interior of the lipid bilayer and they are bound to the membrane surface by noncovalent interaction with other membrane proteins. GPI-linked proteins are proteins which are held on the cell surface by a lipid tail which is inserted into the lipid bilayer.

The term "monoclonal antibody" as used herein refers to an antibody composition having a substantially homogeneous antibody population. It is not intended to be limited as regards to the source of the antibody or the manner in which it is made (e.g. by hybridoma or recombinant synthesis). Monoclonal antibodies are highly specific, being directed against a single antigenic site. In contrast to conventional (polyclonal) antibody preparations which typically include different antibodies directed against different determinants (epitopes), each monoclonal antibody is directed against a single determinant on the antigen.

"A population of monoclonal antibodies" refers to a plurality of heterogeneous monoclonal antibodies, i.e., individual monoclonal antibodies comprising the population may recognize antigenic determinants distinct from each other.

"Immunogen" refers to any substance that induces an immune response. A substance that is an immunogen is described as being "immunogenic". Induction of immune response includes but is not limited to activation of humoral responses (e.g. producing antibodies) or cellular responses (e.g. priming cytotoxic T cells), inflammatory responses (e.g. recruitment of leukocytes), and secretion of cytokines and lymphokines.

The term "heterologous" as applied to a cell used for immunization or transplantation means that the cell is derived from a genotypically distinct entity from the recipient. For example, a heterologous cell may be derived from a different species or a different individual from the same species as the recipient. An embryonic cell derived from an individual of one species is heterologous to an adult of the same species.

A cell is of "ectodermal", "endodermal" or "mesodomal" origin, if the cell is derived, respectively, from one of the three germ layers—ectoderm, the endoderm, or the mesoderm of an embryo. The ectoderm is the outer layer that produces the cells of the epidermis, and the nervous system. The endoderm is the inner layer that produces the lining of the digestive tube and its associated organs, including but not limited to pancreas and liver. The middle layer, mesoderm, gives rise to several organs (including but not limited to heart, kidney, and gonads), connective tissues (e.g., bone, muscles, tendons), and the blood cells.

The terms "medium", "cell culture medium", and "culture medium" are used interchangeably. The terms refer to the aqueous microenvironment in which the mammalian cells are grown in culture. The medium comprises the physicochemical, nutritional, and hormonal microenvironment.

A cell culture medium is "essentially serum-free" when the percentage by volume of serum in the medium does not mask antigenic sites or antibody binding sites on cell surfaces. The term "essentially serum-free" generally applies when the cell culture medium comprises less than about 50% serum (by volume), preferably less than about 25% serum, even more preferably less than about 5% serum, and most preferably less than about 0.1% serum.

A cell surface is "substantially free of serum biomolecules" when at least about 75% of the pancreatic progenitor cell surfaces, more preferably at least about 90% of the pancreatic progenitor cell surfaces, even more preferably at least about 95% of the pancreatic progenitor cell surfaces, and most preferably at least about 99% of the pancreatic progenitor cell surfaces do not have serum biomolecules derived from serum binding to the cell surface such that antigenic sites or antibody binding sites are bound or are unavailable for antigenic recognition by an antibody or a portion of an antibody. Cell surface can determined by measuring the cell size, either by microscopy or flow cytometry. For example, synthetic beads of various known sizes are commonly used for calibration in flow cytometry. A small quantity of calibrated bead may be mixed with pancreatic progenitor cells and the resultant population is analyzed by flow cytometry. Pancreatic progenitor cell can then be compared with the size of the calibrated beads. Calculations of cell surface amount can be accomplished since the sizes of the beads are known.

As used herein, a "substantially pure" population of pancreatic progenitor cells is a population of cells that is comprised at least about 85% pancreatic progenitor cells, preferably at least about 90%, and even more preferably about 95% or more.

A "defined medium" and "basal cell-sustaining medium" are used interchangeably herein and refer to a medium comprising nutritional and hormonal requirements necessary for the survival and/or growth of the cells in culture such that the components of the medium are known. Traditionally, the defined medium has been formulated by the addition of nutritional and growth factors necessary for growth and/or survival. Typically, the defined medium provides at least one component from one or more of the following categories: a) all essential amino acids, and usually the basic set of twenty amino acids plus cystine; b) an energy source, usually in the form of a carbohydrate such as glucose; c) vitamins and/or other organic compounds required at low concentrations; d) free fatty acids; and e) trace elements, where trace elements are defined as inorganic compounds or naturally occurring elements that are typically required at very low concentrations, usually in the micromolar range. The defined medium may also optionally be supplemented with one or more components from any of the following categories: a) one or more mitogenic agents; b) salts and buffers as, for example, calcium, magnesium, and phosphate; c) nucleosides and bases such as, for example, adenosine and thymidine, hypoxanthine; and d) protein and tissue hydrolysates.

As used herein, "conditioned media" refers to culture media, free of intact cells, in which pancreatic epithelial progenitor cells have been grown. Pancreatic cells grown in nutrient media may release factors which promote the continued survival, growth, and maintenance of pre-existing state of pre-differentiation of the pancreatic progenitor cells. Conditioned media may be used to reconstitute a cell pellet or added to cells already existing in culture plates. Conditioned media may also be used alone or to supplement nutrient media being used to feed pancreatic cells. Since conditioned media derived from nutrient media and nutrient media, as described herein, is essential serum-free, conditioned media is also essentially serum-free.

"Standard incubation conditions" refers to the physico-chemical conditions in an incubator designed for tissue culture in which cells are placed. Generally, the standard incubation conditions are about 37 degrees Celsius and about 5% $CO_2$ content with humidification. All tissue culture techniques and equipment should be performed under sterile conditions. Tissue culture containers refer to any type of container that may be used for culturing cells. Non-limiting examples include flasks and plates.

A "mitogenic agent" or "growth factor" is a molecule which stimulates mitosis of the mammalian cells. Generally, the mitogenic agent or growth factor enhances survival and proliferation of mammalian cells in cell culture and is a polypeptide. The mitogenic polypeptide can be a "native" or "native sequence" polypeptide (i.e. having the amino acid sequence of a naturally occurring growth factor) regardless of the method by which it is produced (e.g. it can be isolated from an endogenous source of the molecule or produced by synthetic techniques including recombinant techniques), or a variant or mutant thereof (see definition below). Non-limiting examples include activators of one or more members of the erbB receptor family; agents which elevate cAMP levels in the culture medium (e.g. forskolin, cholera toxin, cAMP or analogues thereof); adhesion molecules such as neural cell adhesion molecule (N-CAM), laminin or fibronectin; progesterone; neurotrophic factors such as bone-derived neurotrophic factor (BDNF) and ciliary neuronotrophic factor (CNTF); neurotrophin-3, -4, -5, or -6; platelet-derived growth factor (PDGF); fibroblast growth factor such as acidic FGF (aFGF) and basic FGF (bFGF); vascular endothelial growth factor (VEGF); transforming growth factor (TGF) such as TGF-α and TGF-β; insulin-like growth factors, including IGF-I and IGF-II; hormones such as estrogen, testosterone, thyroid hormone, insulin and any of those mitogens listed in Table 8.2 at pages 138–139 of Mather, J. P. and Roberts, P. E. (1998) "Introduction to Cell and Tissue Culture", Plenum Press, New York.

"Pancreatic progenitor cell aggregates", "pancreatic progenitor cell spheres", and "pancreatic cell clusters" are used interchangeably throughout and refers to a mass of a plurality of pancreatic progenitor cells which can form a three-dimensional structure resembling roughly a sphere.

A "grafting recombinant", as used herein, refers to the combined unit of pancreatic progenitor cell aggregates placed with mesenchymal tissue. Mesenchymal tissue can be of pancreatic or non-pancreatic origin. Mesenchymal tissue can be from a species heterologous to the graft recipient. Mesenchymal tissue can also be from a species heterologous to the source of pancreatic progenitor cells. Grafting recombinants can be incubated on substrate, preferably a soft, biological substrate (e.g. agar) for a period ranging from 1 hour to 72 hours, more preferably between 6 hours to 24 hours, and even more preferably, overnight with an incubation period of about 8 to 16 hours. Olumi A. F., et. al. Cancer Research 59, 5002–5011, (1999).

"Serum", as used herein, refers to the fluid phase of mammalian blood that remains after blood is allowed to clot.

"Serum biomolecules", as used herein, refers to biological compositions found in serum. Examples include, but are not limited to, albumin, α1-globulin, α2-globulin, β-globulin, and δ-globulin. Serum biomolecules can include biological compositions, whole or partial, that are either naturally found in serum or derived from processing and handling of serum.

The terms "mammals" or "mammalian" refer to warm blooded vertebrates which include but are not limited to humans, mice, rats, rabbits, simians, sport animals, and pets.

Isolation and Maintenance of Pancreatic Progenitor Cells

Pancreatic progenitor cells of this invention are isolated from human fetal pancreatic tissue. The age of the fetus is between about week 6 and about week 40, preferably between about week 8 and about week 26, and even more preferably between about week 12 and about week 22. The pancreatic tissue can be identified by gross anatomy, outward appearance, and location within the fetus. Several features of gross anatomy and appearance distinguishing a pancreas are: an elongated lobulated retroperitoneal gland, lack of capsule, and extension from the concavity of the duodenum of the intestine to the spleen. The pancreas consists of a flattened head or caput within the duodenal concavity, an elongated three-sided body extending transversely across the abdomen, and a tail in contact with the spleen. Once identified, fetal pancreatic tissue is microdissected. The purpose of microdissection is to separate structures containing epithelial cells from connective tissue and non-pancreatic tissue such as fat, membranes, etc. or to separate cells from each other. Non-limiting examples of microdissection include devices that render mechanical shearing forces (i.e. homogenizer, mortar and pestle, blender, etc.), devices that render cuts or tears (i.e. scalpel, syringes, forceps, etc.), or ultrasonic devices. Alternatively, another method of microdissecting fetal pancreatic tissue is the use of enzyme treatment. Various enzyme treatments used to microdissect tissue are well known in the art. One method includes the use of collagenase-dispase to digest partially sheared pancreatic tissue in a buffered medium that will sustain viability of cells isolated from the pancreatic tissue. A concentration of at least about 0.5 mg/ml collagenase-dispase is used, more preferably at least about 1 mg/ml and even more preferably at least about 5 mg/ml. The amount of enzyme will depend on the age of the fetus and how large the pancreatic tissue is. In the preferred embodiment, pancreatic tissue from fetus between about 14 weeks and about 22 weeks is digested with about 5 mg/ml of collagenase-dispase. A wide variety of basal cell-sustaining media that can be used to keep the pH of the liquid in a range that promotes survival of pancreatic progenitor cells and to provide additional volume of liquid within which the enzymatic digestion can occur. Non-limiting examples include F12/DMEM, Ham's F10 (Sigma), CMRL-1066, Minimal essential medium (MEM, Sigma), RPMI-1640 (Sigma), Dulbecco's Modified Eagle's Medium (DMEM, Sigma), and Iscove's Modified Eagle's Medium (IMEM). In addition, any of the basal nutrient media described in Ham and Wallace *Meth. Enz.*, 58:44 (1979), Barnes and Sato *Anal. Biochem.*, 102:255 (1980), or Mather, J. P. and Roberts, P. E. "Introduction to Cell and Tissue Culture", Plenum Press, New York (1998) can also be used. Examples of other enzymes that could be used to digest tissue include neutral proteases, serine proteases including, but not limited to, trypsin, chymotrypsin, elastase, collagenase, and thermolysin. In another preferred embodiment, enzymes that digest DNA, such as DNAase, are used to cut the DNA into smaller pieces in order to prevent tissue aggregation by free DNA. Treatment of fetal pancreatic tissue with enzyme results in cell yields of various amounts. Some cells are in single cell suspensions, others are in cell aggregates. Cells not associated with solid tissue matter can be separated from each other or from solid tissue matter or from debris by using a density gradient. Compounds that can be used to create a density gradient include, but are not limited to, serum (i.e. bovine serum albumin or BSA), ovalbumin, nonionic synthetic polymers of sucrose (i.e. Ficoll™), colloidal polyvinylpyrrolidone-coated silica (i.e. Percoll™), polyvinylpyrrolidone or PVP, and methylcellulose. In a preferred embodiment, density gradients that are capable of neutralizing the enzymes used to digest pancreatic tissues are used. One example of such a density gradient is BSA. The amount of BSA used is about 50% volume-to-volume ratio, more preferably about 25%, more preferably about 10%, and even more preferably about 5%. The amount of debris that needs to be removed depends on several factors, such as the extent of digestion or mechanical shear forces applied to the pancreatic tissue. In some cases, one density gradient is enough to remove debris (e.g. mesenchymal tissue, fatty particles, or broken cell membranes). In other cases, more than one application of a density gradient will be needed. The desired product is a population of relatively pure pancreatic cell aggregates.

Pancreatic cells are then resuspended in a basal cell-sustaining media. A variety of basal cell-sustaining media is available for use. Examples include, but are not limited to, Ham's F12 medium, RPMI-1640, and CMRL-1066. For more optimal conditions to promote pancreatic progenitor cell survival and growth, a variety of nutrients may be added to supplement the basal media. Examples include, but are not limited to, insulin, transferrin, epidermal growth factor, ethanolamine, phosphoethanolamine, selenium, triiodothyronine, progesterone, hydrocortisone, forskolin, heregulin, aprotinin, bovine pituitary extract, and gentamycin. In a preferred embodiment, the following amounts of nutrients are used to promote pancreatic progenitor cell survival and growth: at least about 1 $\mu$g/ml insulin and not more than about 100 $\mu$g/ml insulin, more preferably about 10 $\mu$g/ml insulin; at least about 1 $\mu$g/ml transferrin and not more than about 100 $\mu$g/ml transferrin, more preferably about 10 $\mu$g/ml transferrin; at least about 1 ng/ml epidermal growth factor and not more than about 100 ng/ml epidermal growth factor, more preferably about 5 ng/ml epidermal growth factor; at least about $1\times10^{-8}$ M ethanolamine and not more than about $1\times10^{-2}$ M ethanolamine, more preferably about $1\times10^{-6}$ M ethanolamine; at least about $1\times10^{-9}$ M phosphoethanolamine and not more than about $1\times10^{-1}$ M phosphoethanolamine, more preferably about $1\times10^{-6}$ M phosphoethanolamine; at least about $1\times10^{-12}$ M selenium and not more than about $1\times10^{-1}$ M selenium, more preferably about $1\times10^{-8}$ M selenium; at least about $1\times10^{-15}$ M triiodothyronine and not more than about $1\times10^{-1}$ M triiodothyronine, more preferably about $1\times10^{-12}$ M triiodothyronine; at least about $1\times10^{-12}$ M progesterone and not more than about $1\times10^{-1}$ M progesterone, more preferably about $1\times10^{-9}$ M progesterone; at least about $1\times10^{-15}$ M hydrocortisone and not more than about $1\times10^{-1}$ M hydrocortisone, more preferably about $1\times10^{-9}$ M hydrocortisone; at least about 0.001 $\mu$M forskolin and not more than about 50 $\mu$M forskolin, more preferably about 1 $\mu$M forskolin; at least about 0.1 nM heregulin and not more than about 100 nM heregulin, more preferably about 10 nM heregulin,; at least about 1 $\mu$g/ml aprotinin and not more than about 100 $\mu$g/ml aprotinin, more preferably about 25 $\mu$g/ml aprotinin; at least about 1 $\mu$g/ml bovine pituitary extract and not more than about 500 $\mu$g/ml bovine pituitary extract, more preferably about 75 $\mu$g/ml bovine pituitary extract; at least about 1 $\mu$g/ml gentamycin and not more than about 1 mg/ml gentamycin, more preferably about 100 $\mu$g/ml gentamycin. The pancreatic progenitor cells may be grown on different substrates, depending on the type of physical orientation of the cells desired. Non-limiting examples of substrates that may be used include fibronectin, laminin, collagen, polylysine, nitrocellulose, nylon, and polytetrafluoroethylene. In one embodiment, pancreatic progenitor cells are grown on fibronectin-coated tissue culture plates in the preferred nutrient media described above. Pancreatic progenitor cells form cell aggregates when cultured in the preferred nutrient media in fibronectin-coated plates. Further, this culturing combination allows for separation of undesired mesenchymal cells and pancreatic progenitor aggregates. In a preferred embodiment, purification of pancreatic cell aggregates is readily accomplished by culturing the pancreatic progenitor cells in preferred media using CMRL 1066 as a basal media in a fibronectin plate. Pancreatic progenitor cells form large, round clusters of cells that are non-adherent while other cell types (i.e. mesenchymal cells) adhere to the fibronectin coating. The clusters of pancreatic progenitor cells may then be collected and transferred to another tissue culture container for subculturing and proliferation. When proliferation of more pancreatic progenitor cell clusters is desired, the tissue culture container is coated with fibronectin and the pancreatic progenitor cells are cultured in the preferred media disclosed herein using CMRL 1066 as a basal media. In another embodiment, pancreatic progenitor cells are grown in the preferred nutrient media using F12/DMEM as a basal media in collagen-coated tissue culture containers. Pancreatic progenitor cells form monolayers in this embodiment.

The frequency of feeding pancreatic progenitor cells may be once a day or every other day. In one embodiment, pancreatic progenitor cells may be fed by replacing the entirety of the old nutrient media with new nutrient media. In another embodiment, pancreatic progenitor cells may be fed with conditioned media in which these cells were grown. Subculturing pancreatic progenitor cells to obtain a greater number of cells is accomplished by taking pancreatic progenitor cells in cluster form (grown on fibronectin) or in monolayer form (grown on collagen) and dividing the plurality of cells into multiple tissue culture containers. Nutrient media is then added to each of the tissue culture containers to achieve a lower concentration of pancreatic progenitor cells than in the original tissue culture container. The nutrient media that is added is dependent on the type of pancreatic progenitor cell arrangement desired. When monolayer arrangement is desired, then F12/DMEM is used a basal media in the preferred nutrient media disclosed herein coupled with collagen coating in the tissue culture containers. When pancreatic cell clusters are desired, CMRL 1066 is used a basal media in the preferred nutrient media disclosed herein coupled with fibronectin coating in the tissue culture containers. Because the claimed pancreatic progenitor cells are unique to this invention and will secrete factors specific to these cells, the conditioned media derived from the pancreatic progenitor cells are also unique. In this invention, pancreatic progenitor cells form aggregates when grown in the preferred nutrient media, defined above, in fibronectin tissue culture plates. When the substrate is collagen-coated tissue culture plates, pancreatic progenitor cells form an attached stromal monolayer. Addition of conditioned media promotes greater vitality in the pancreatic progenitor cells. A preferred amount of conditioned media is at least about 1% to at least about 25% of total media volume. An even more preferred amount of conditioned media is about 15% of total media volume. A frequency of feeding that is preferable for promoting the survival and growth of pancreatic progenitor cells is once a week, even more preferable is twice a week, and most preferably every other day. The pancreatic progenitor cells of this invention can be passaged multiple times while retaining dividing capability and without inducing differentiation of these pancreatic progenitor cells into terminally differentiated acinar, islet, or ductal cells.

Characterization of Pancreatic Progenitor Cells

Figure 8:
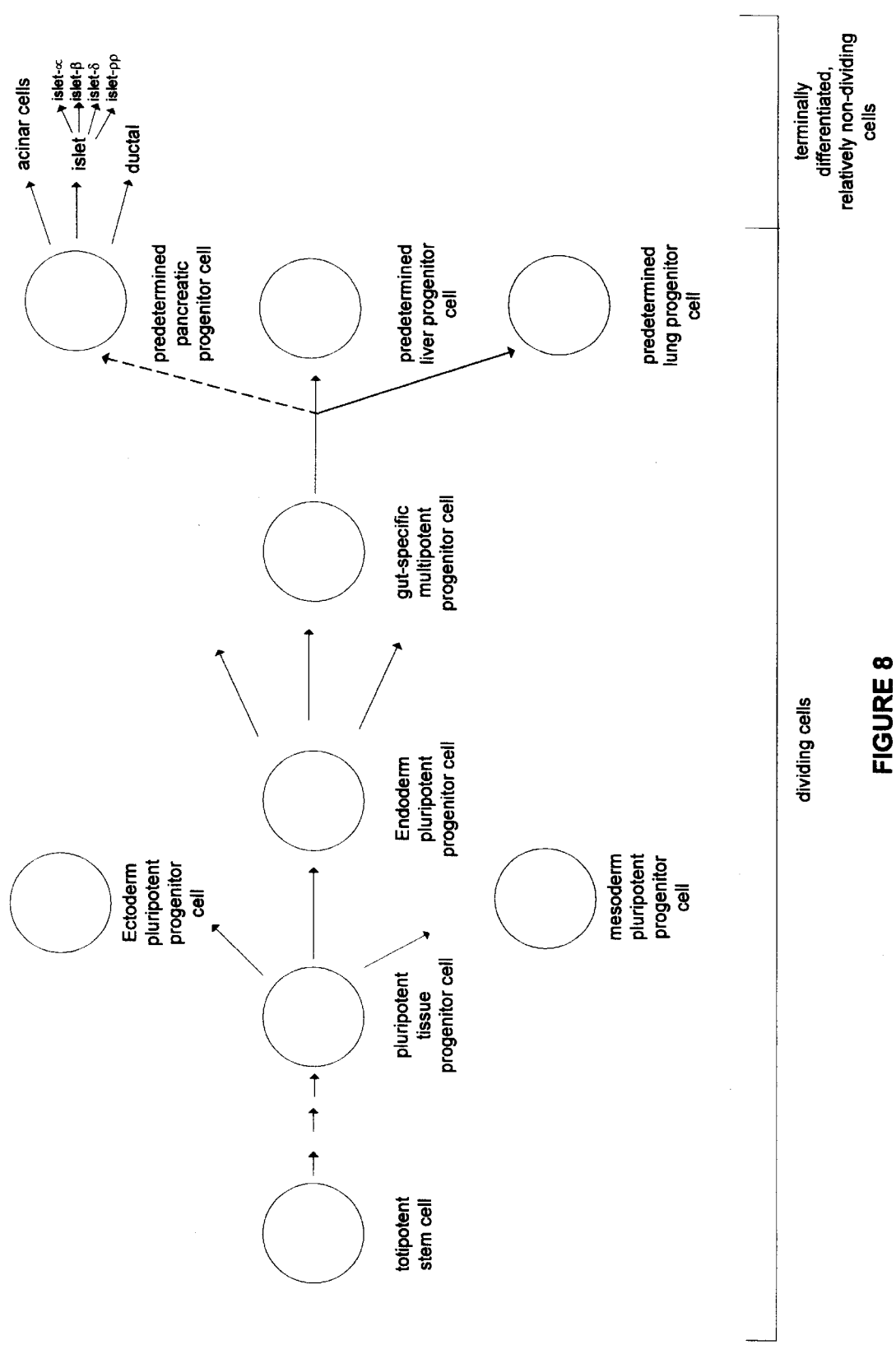
FIG. 8 is a schematic depiction of the development of a pancreatic cells from a totipotent stem cell. The dotted line indicates the stage of differentiation at which the human pancreatic progenitor cell of this invention resides.

The population of pancreatic progenitor cells of this invention isolated in the manner disclosed herein have several defining characteristics. First, the pancreatic progenitor cells are at a stage that can be described as "pre-determined pancreatic". Of the gut-specific progenitor cells, some are pre-determined to become pancreatic cells. It is at this stage of development that the population of pancreatic progenitor cells claimed herein resides (FIG. 8). The pancreatic progenitor cells of this invention have the capacity to become either exocrine or endocrine cells. Endocrine and exocrine cells, as used herein, are defined by their secretions. Endocrine cells, such as α-islet cells and β-islet cells secrete glucagon and insulin, respectively. Exocrine cells, such as acinar cells, secrete a variety of pancreatic digestive juices such as trypsinogen, α-amylase, and lipases.

Identification of pancreatic progenitor cells may be accomplished by morphology or specific markers or a combination of both techniques. As disclosed herein, pancreatic progenitor cells can be rounded and cyst-like in appearance or elongated in a monolayer formation depending on the culture conditions in which the pancreatic progenitor cells are grown. Identification of differentiated pancreatic progenitor cells may also be accomplished by morphology. Morphology of islet cells is an ovoid shape, about 75 $\mu$m to 175 $\mu$m in size (long axis). Islet cells tend to be located more towards the tail end of a pancreas (away from the duodenal cavity). Markers that can be used to detect islet cells include but are not limited to glucagon for islet-α cells, insulin for islet-β cells, somatostatin for islet-δ cells, and pancreatic polypeptide for islet-PP cells. Markers that can be used to detect ductal cells include, but are not limited to, cytokeratins (CK) 7, CK 8, CK 18, CK 19, mucin MUC1, carbonic anhydrase II, and carbohydrate antigen 19.9 (sialyl-Lewis-a). Morphology of ductal cells is small, round, approximately 10 $\mu$m across the cell, appears to be a tightly packed, cuboidal epithelium. Morphology of acinar cells include a larger size than ductal cells, shape, and zymogen granules present within acinar cells. Markers that can be used to identify acinar cells include but are not limited to carboxypeptidase A and amylase.

Ki67 or PCNA are markers that can be used to determine proliferation of pancreatic progenitor cells. Pre-determined pancreatic progenitor cells are still capable of dividing whereas terminally differentiated exocrine or endocrine cells are essentially non-dividing. Staining with Ki67 or PCNA can determine proliferative state of a pancreatic cell under analysis.

Pancreatic progenitor cells of this invention are maintained at their pre-existing pre-differentiation state in serum-free media. Basal cell-sustaining media or the preferred nutrient media disclosed herein or conditioned media may be used to culture the pancreatic progenitor cells in vitro. Different types of substrate on tissue culture plates can be used to obtain either aggregates or monolayers of pancreatic progenitor cells. The use of fibronectin in conjunction with the preferred nutrient media disclosed herein results in aggregates of pancreatic progenitor cells whereas the use of collagen on tissue culture plates results in monolayers of pancreatic progenitor cells.

Pancreatic progenitor cells of this invention have the capacity to be passaged multiple times in the preferred serum-free nutrient media disclosed herein. Multipotency is retained during each passage and at any point after each passage, pancreatic progenitor cells of this invention can differentiate into functional exocrine or endocrine cells. In addition, at any point after each passage, pancreatic progenitor cells may be used as an immunogen, for cell therapy, for bioassays, to establish a human pancreatic model, or for drug discovery and/or development as disclosed herein.

Another characteristic of the pancreatic progenitor cells of this invention is the capacity to differentiate into exocrine or endocrine cells upon transplantation under kidney capsule of a recipient mammal. Prior to transplantation, pancreatic progenitor cells do not make digestive enzymes, such as amylase or lipase, and will not stain positive for digestive enzymes. As disclosed herein, pancreatic progenitor cells can be grown either in pancreatic progenitor cell aggregates or in monolayers and then combined with mesenchymal tissue and placed under a kidney capsule of a recipient mammal. Preferably, human pancreatic progenitor cell aggregates are combined with rat seminal vesicle mesenchymal tissue and placed under the kidney capsule of a recipient mammal. A portion of the transplant may be removed for analysis using the markers, morphology, or a combination thereof to identify the pancreatic cells.

Antibodies, either monoclonal or polyclonal, which can be used to identify this population of pancreatic progenitor cells include, but are not limited to, anti-cytokeratin 19, anti-carcinoembryonic antigen (CEA), anti-carbonic anhydrase II, anti-cystic fibrosis transmembrane conductance regulator (CFTR).

Uses of Pancreatic Progenitor Cells

Uses as an Immunogen

A use for pancreatic progenitor cells is as an immunogen. As disclosed in this invention, the unique serum-free culturing conditions allow the cell surfaces of the pancreatic progenitor cells to remain free of serum proteins or serum biomolecules that may bind to the surface. A potential problem of antigenic sites that may be "masked" with binding by serum biomolecules is avoided by using the disclosed serum-free isolation and culturing techniques. Accordingly, a panel of antibodies may be generated to newly available antigens that were "masked" when using culture conditions containing serum.

Pancreatic progenitor cells isolated and cultured with the methods disclosed herein can be used as an immunogen that is administered to a heterologous recipient. Administration of pancreatic progenitor cells as an immunogen can be accomplished by several methods. Methods of administrating pancreatic progenitor cells as immunogens to a heterologous recipient include but are not limited to: immunization, administration to a membrane by direct contact such as swabbing or scratch apparatus, administration to mucous membrane by aerosol, and oral administration. As is well-known in the art, immunization can be either passive or active immunization. Methods of immunization can occur via different routes which include but are not limited to intraperitoneal injection, intradermal injection, local injection. Subjects of immunization may include mammals such as mice. The route and schedule of immunization are generally in keeping with established and conventional techniques for antibody stimulation and production. While mice are employed in this embodiment, any mammalian subject including humans or antibody producing cells therefrom can be manipulated according to the processes of this invention to serve as the basis for production of mammalian hybridoma cell lines. Typically, mice are inoculated intraperitoneally or in alternate regions (i.e. footpad, tail base, etc.) with an immunogenic amount of the pancreatic progenitor cells and then boosted with similar amounts of the immunogen. In an alternative, cells grown on non-biological membrane matrix, are surgically implanted intraperitoneally into the host mammal. Lymphoid cells, preferably spleen lymphoid cells from the mice, are collected a few days after the final boost and a cell suspension is prepared therefrom for use in the fusion.

Hybridomas are prepared from the lymphocytes and immortalized myeloma cells using the general somatic cell hybridization technique of Kohler, B. and Milstein, C. Nature 256:495–497 (1975) as modified by Buck, D. W., et al., In Vitro, 18:377–381 (1982). Available myeloma lines, including but not limited to X63-Ag8.653 and those from the Salk Institute, Cell Distribution Center, San Diego, Calif., USA, may be used in the hybridization. The technique involves fusing the myeloma cells and lymphoid cells using a fusogen such as polyethylene glycol, or by electrical means well known to those skilled in the art. After the fusion, the cells are separated from the fusion medium and grown in a selective growth medium, such as HAT medium, to eliminate unhybridized parent cells. Any of the media described herein can be used for culturing hybridomas that secrete monoclonal antibodies. As another alternative to the cell fusion technique, EBV immortalized B cells are used to produce the monoclonal antibodies of the subject invention. The hybridomas are expanded and subcloned, if desired, and supernatants are assayed for anti-immunogen activity by conventional immunoassay procedures (e.g., radioimmunoassay, enzyme immunoassay, or fluorescence immunoassay).

Hybridomas that produce such antibodies may be grown in vitro or in vivo using known procedures. The monoclonal antibodies may be isolated from the culture media or body fluids, by conventional immunoglobulin purification procedures such as ammonium sulfate precipitation, gel electrophoresis, dialysis, chromatography, and ultrafiltration, if desired. Undesired activity if present, can be removed, for example, by running the preparation over adsorbents made of the immunogen attached to a solid phase and eluting or releasing the desired antibodies off the immunogen.

In this manner, a panel of novel antibodies to cell surface antigen specific to a stage of pancreatic progenitor cells can be generated using the pancreatic progenitor cells of this invention. Once monoclonal antibodies to cell surface antigens on pancreatic progenitor cells are made by the method disclosed herein, the antibodies can be used to for several uses. The antibodies may be sequenced and cloned for purposes of generating recombinant antibodies or humanized antibodies. Other uses of pancreatic progenitor cell-specific antibodies include but are not limited to biological testing or purification (i.e. isolating pancreatic progenitor cells by methods such as flow cytometry and panning), therapeutic uses (i.e. promoting or arresting cell growth by binding of antibody to target cell or promoting or arresting growth of a cell mass by binding of antibody to target cell), clinical diagnosis, and biological markers (i.e. identification of other pancreatic or non-pancreatic cells).

Another use as an immunogen is to modulate overall immune response in a heterologous recipient. As is well-documented in the art, foreign substances such as cells or organs introduced into a heterologous recipient may induce a variety of immune responses. The immune responses can be in the form of rejection (e.g. in organ transplantation), T cell activation (e.g. cross-priming), anergy, or tolerance. The overall immune response can be systemic or localized. In the case where a localized immune response is desired, for example in the gut region, an immunogen such as pancreatic progenitor cells is introduced into the gut region in an effective amount. Effective amount can be determined in a stepwise fashion in which increasing amounts of pancreatic progenitor cells are introduced into a heterologous recipient and the subsequent immune response is monitored. Overall immune response (e.g. antibody production, cytokine production, T cell proliferation, anergy, tolerance, etc.) may be monitored by a number of methods including but not limited to ELISA, proliferation assays, flow cytometry with cell surface markers, and immunohistochemistry.

Use of Pancreatic Progenitor Cells for Drug Discovery

Another use of pancreatic progenitor cells is related to drug discovery. Since the pre-differentiated multipotent pancreatic progenitor cell population has not been isolated and cultured in the disclosed manner, the pancreatic progenitor cell population may secrete proteins that have not been heretofore discovered or characterized. Previous culturing techniques using serum may inhibit the secretion of proteins. Alternatively, proteins may change in function, conformation, or activity as they are being secreted and interacting with serum biomolecules. Proteins secreted by pancreatic progenitor cells have minimal interference from serum biomolecules and thus, may be more physiologically and topologically accurate. Therefore, proteins secreted by pancreatic progenitor cells may be used as targets for drug development. In one embodiment, drugs can be made to target specific proteins on pancreatic progenitor cells in vivo. Binding of the drug may promote differentiation of the pancreatic progenitor cells into specific sub-pancreatic cells, such as islet cells. This approach may be useful when islet cell neogenesis is desired, for example in treatment for diabetes. In another embodiment, drug specific for regulatory proteins of pancreatic progenitor cells may be used to arrest growth of a particular type of cell, for example in cases of cystic fibrosis wherein acinar cells are being replaced by ductal cells. In another embodiment, a drug may be an inhibitor of the growth of stem cells or cancer cells which express fetal antigens. Any of these proteins can be used as targets to develop therapeutic antibody, protein, or small molecule drugs.

Uses of Pancreatic Progenitor Cells for Cell Therapy

In another use, pancreatic progenitor cell lines are used for cell therapy. Transplantation of pancreatic progenitor cells is one such example of cell therapy. In cases where different types of pancreatic cells, such as islet cells or acinar cells, are unable to perform their function of secreting insulin or glucagon respectively, transplantation of pancreatic progenitor cells provides a remedy because the pancreatic progenitor cells of this invention are multipotent and can differentiate into functional exocrine and endocrine cells. To practice this use, pancreatic progenitor cells are isolated and cultured in serum-free, nutrient-defined media using the methods disclosed. Pancreatic progenitor cells are grown on fibronectin-coated tissue culture plates to obtain pancreatic progenitor cell aggregates. Pancreatic progenitor cell aggregates are grown under standard incubation conditions for about half a day to about 7 days, more preferably for about 1 day to about 5 days, and even more preferably about 3 days. Pancreatic cell aggregates can then be administered to a recipient and allowed to differentiate. In an alternative, pancreatic cell aggregates can be used as cellular carriers of gene therapy wherein pancreatic cells are transfected with one or more genes and enclosed in a delivery device and then administered to a recipient. In another embodiment, pancreatic cell aggregates are placed under a kidney capsule and allowed to differentiate into acinar, ductal, or islet cells. In another embodiment, pancreatic cell aggregates are used in a device which contains cells and limits access from other cells (i.e. Theracyte®) to limit immune system responses.

Uses of Pancreatic Progenitor Cells to Make Human Tissue Models

Another use for pancreatic progenitor cells is to create human tissue models in non-human mammals. Pancreatic progenitor cell aggregates are placed on top of mesenchymal tissue to form grafting recombinants. To form grafting recombinants, about 1 to 15 pancreatic cell spheres, more preferably about 5 to 8 pancreatic cell spheres, are placed on top of mesenchymal tissue. The mesenchymal tissue may be either pancreatic or non-pancreatic tissue and may be derived from a different species from which pancreatic progenitor cells are isolated. In a working example, human pancreatic progenitor cells are placed on top of rat mesenchymal seminal vesicle tissue to form a graft recombinant. A skilled artisan may determine the optimal combination in a stepwise fashion, by first isolating human pancreatic progenitor cells using the methods disclosed herein and then combining with mesenchymal tissue from different organs. In some embodiments, a different species, e.g. rat, is used as a source for mesenchymal tissue in combination with human pancreatic progenitor cells. The use of heterologous species allows human-specific markers to be used to determine the identity of differentiated pancreatic cells. The likelihood of false positives is reduced if rat mesenchymal tissue is used. Likewise, the use of seminal vesicle mesenchymal tissue over pancreatic mesenchymal tissue reduces the likelihood of false positives in identifying differentiated pancreatic cells. In a preferred embodiment, about 1 to 12 pancreatic progenitor cell spheres, even more preferably about 5 to 8 pancreatic progenitor cell spheres, are placed on top of rat seminal vesicle mesenchymal tissue. Preferably, about $1 \times 10^4$ to about $5 \times 10^6$ mesenchymal cells are used. Even more preferably, about $2 \times 10^5$ to about $5 \times 10^5$ mesenchymal cells are used. A graft recombinant comprising pancreatic progenitor cell spheres placed on mesenchymal tissue is then placed under the kidney capsule, in the fat pad, subcutaneously, or in a device which contains the pancreatic progenitor cells but limits access of other cells to the pancreatic progenitor cells (i.e. Theracyte®) in the recipient mammal. Possible recipient mammals include but are not limited to mice and rats. Typically in graft situations, donor tissue is vulnerable to attack by the recipient's immune system. To alleviate graft rejection, several techniques may be used. One method is to irradiate the recipient with a sub-lethal dose of radiation to destroy immune cells that may attack the graft. Another method is to give the recipient cyclosporin or other T cell immunosuppressive drugs. With the use of mice as recipient mammals, a wider variety of methods are possible for alleviating graft rejection. One such method is the use of an immunodeficient mouse (nude or severe combined immunodeficiency or SCID). In a working example, human pancreatic progenitor cell spheres are placed on rat seminal vesicle mesenchymal tissue and placed under the kidney capsule of an immunodeficient mouse. The graft recombinant remains in the recipient for about 1 to about 52 weeks, preferably about 5 to about 40 weeks, and even more preferably about 6 to about 8 weeks before the grafts are harvested and analyzed for pancreatic progenitor cell differentiation. In some cases, a small portion of the graft is needed for analysis. Markers specific for the islet cells (i.e. insulin, glucagon, etc.), ductal cells (i.e. CK 19, etc.), and acinar cells (i.e. amylase, etc.) is utilized in an immunohistochemical analysis. Another set of markers for exocrine and endocrine functions, such as markers specific for insulin or glucagon, may also be used to analyze the efficacy of the transplantation. These markers can be used separately or in combination with each other. In addition, a combination of one or more of these markers may be used in combination with cell morphology to determine the efficacy of the transplantation.

In one embodiment, human pancreatic model can be generated in a SCID (severe combined immunodeficiency) mouse. This human pancreatic model can be made by utilizing the human pancreatic progenitor cells isolated and cultured with methods disclosed herein and using the human pancreatic progenitor cells to make graft recombinants. Graft recombinants are then placed under the kidney capsule of mice. After about 1 to 10 weeks, preferably about 6 to 8 weeks after implantation under the kidney capsule, the graft or portion thereof is harvested and analyzed by immunohistochemistry. Markers specific to exocrine or endocrine function, such as insulin or glucagon are used to analyze the efficacy of the tissue model system. Alternatively, markers specific for pancreatic tissue such as islet cells (i.e. PDX-1), acinar cells (i.e. amylase), ductal cells (i.e. CK 19) are used. Yet another way to assess the results of pancreatic progenitor cell differentiation is by morphology. Pancreatic progenitor cells have the appearance of being small and round, about 10 μm across the cell, and in a highly compacted columnar epithelium form. Acinar cells have the appearance of large clusters forming acini. Ductal cells have the appearance of small, round, about 40 μm across the cell, and a compacted, cuboidal columnar epithelium. Islet cells have the appearance of epithelial islands surrounded by acinar exocrine units. Further, morphology is combined with functional markers for insulin and glucagon and cell surface markers for specific cells for a more complete assessment. The recombinant tissues thus represent a fully human mini-pancreas in a mouse. These human pancreatic tissue models can be used to assess efficacy and toxicity of drug candidates being developed to treat type I and type II diabetes, pancreatitis, pancreatic cancer, and for other pancreatic insufficiencies. They can also be used to screen any drug for pancreatic toxicity. In a further use, the recipient animal would undergo surgical or chemical (i.e. streptazoticin) pancreatic or islet-β cell ablation so the insulin being produced is coming from the graft.

Uses of Pancreatic Progenitor Cells in Bioassays

The pancreatic progenitor cells disclosed herein can be used in various bioassays. In one use, the pancreatic progenitor cells are used to determine which biological factors are required for differentiation. By using the pancreatic progenitor cells in a stepwise fashion in combination with different biological compounds (such as hormones, specific growth factors, etc.), one or more specific biological compounds can be found to induce differentiation to islet cells. Employing the same stepwise combinations, one or more specific biological compound can be found to induce differentiation to acinar cells and likewise for ductal cells. Other uses in a bioassay for pancreatic progenitor cells are differential display (i.e. mRNA differential display) and protein-protein interactions using secreted proteins from pancreatic progenitor cells. Protein-protein interactions can be determined with techniques such as yeast two-hybrid system. Proteins from pancreatic progenitor cells can be used to identify other unknown proteins or other cell types that interact with pancreatic progenitor cells. These unknown proteins may be one or more of the following: growth factors, hormones, enzymes, transcription factors, translational factors, and tumor suppressors. Bioassays involving pancreatic progenitor cells and the protein-protein interaction these cells form and the effects of protein-protein or even cell-cell contact may be used to determine how surrounding tissue, such as mesenchymal tissue, contributes to pancreatic progenitor cell differentiation.

The following examples provide a detailed description of the isolation, characterization, and use of pancreatic progenitor cells. These examples are not intended to limit the invention in any way.

EXAMPLES

Example 1
Isolation of Pancreatic Progenitor Cells

Fetal pancreas (gestational age 14–22 weeks) was mechanically pulled apart by microdissection under a stereo microscope prior to enzymatic dissociation. Enzyme treatment consisted of placing the partly dissociated tissue in 1 ml F12/DMEM medium containing 5 mg/ml collagenase-dispase, 20 μg/ml soybean trypsin inhibitor and 50 μg/ml DNAase for 15 minutes at 37 degrees Celsius.

Cell aggregates were layered on top of a 5% (by volume) BSA gradient and washed by centrifugation for 6 minutes at 900 rpm. Pelleted cells which were still in aggregate form were resuspended in growth medium consisting of CMRL 1066 nutrient medium containing the following factors:

| | |
|---|---|
| Insulin | 10 μg/ml |
| Transferrin | 10 μg/ml |
| Epidermal growth factor | 5 ng/ml |
| Ethanolamine | $10^{-6}$ M |
| Phosphoethanolamine | $10^{-6}$ M |
| Selenium | $2.5 \times 10^{-8}$ M |
| Triiodothyronine | $10^{-12}$ M |
| Progesterone | $10^{-9}$ M |
| Hydrocortisone | $10^{-9}$ M |
| Forskolin | 1 μM |
| Heregulin | 10 nM |
| Aprotinin | 25 μg/ml |
| Bovine pituitary extract | 75 μg/ml |
| Gentamycin | 100 μg/ml |

Figure 2:
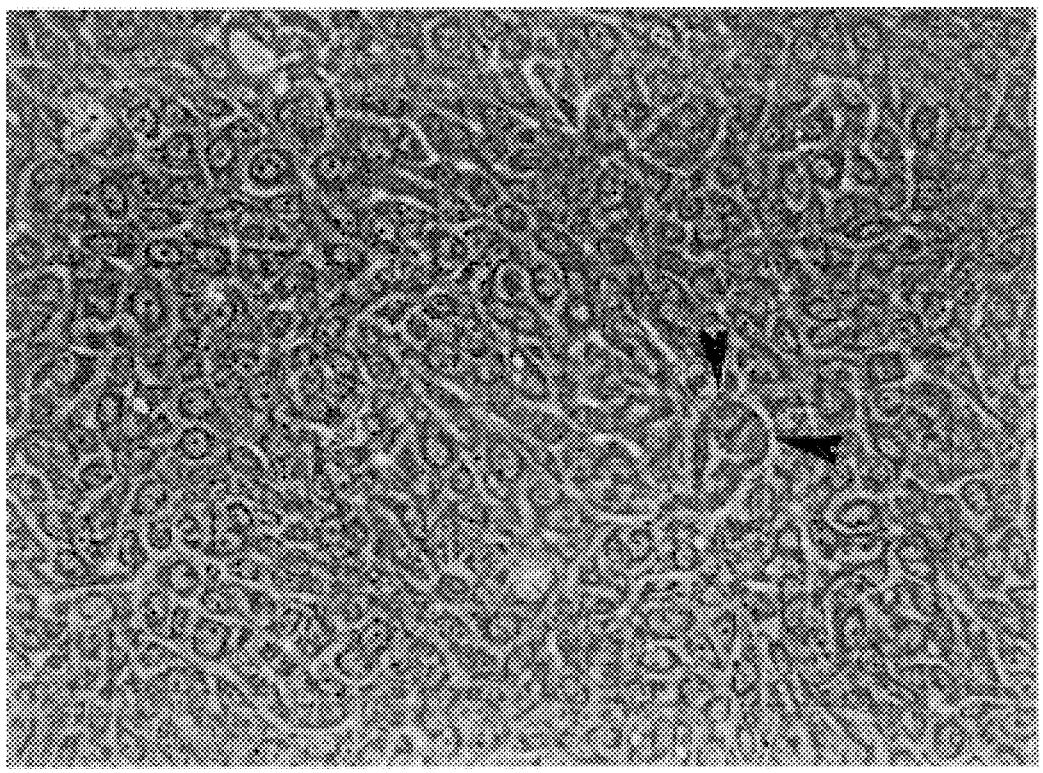
FIG. 2 shows human pancreatic epithelial cells grown on collagen-coated plates after three passages. The arrows denote dividing cells.

Resuspended cell aggregates were aliquoted into fibronectin-coated wells (6–12) of a 24-well dish and incubated at 37 degrees Celsius in a humidified 5% $CO_2$ incubator for 72 hours. After 72 hours, the epithelial cells formed suspended spherical structures (FIG. 1A) and the mesenchymal or stromal cells were attached to the surface of the well. When monolayer formation was desired, the pancreatic aggregates or pancreatic spheres from 6 of the wells were collected with a micropipet and placed on a collagen-coated 60 mm dish using F12/DMEM as basal nutrient media with the nutrients supplements as disclosed. Within 24 hours, the structures attached and the cells from the structure spread out onto the collagen to form an epithelial monolayer (FIG. 1B). These pancreatic progenitor cells could be passaged at least three times (FIG. 2).

Example 2
Use of Pancreatic Progenitor Cells in Transplants

For the purpose of recombinant grafting, the cells were left in the spherical state from the time of original plating or the monolayers were released from the collagen and grown in non-coated flasks where they remained in suspension and re-aggregated into spherical structures.

For the purpose of grafting, the spheres were placed on top of seminal vesicle mesenchyme from e15 rats, usually 5–8 spheres to a mesenchyme aggregate of $2 \times 10^5$ to $5 \times 10^5$ cells. Each recombinant was placed on agar and incubated overnight at 37 degrees in a 5% $CO_2$ humidified chamber.

The grafting consisted of placing from 3–6 recombinants under the kidney capsule or fat pad of an immunodeficient mouse (nude or SCID) and left for 6–8 weeks. The grafts were then harvested and processed for immunohistochemistry.

Figure 3:
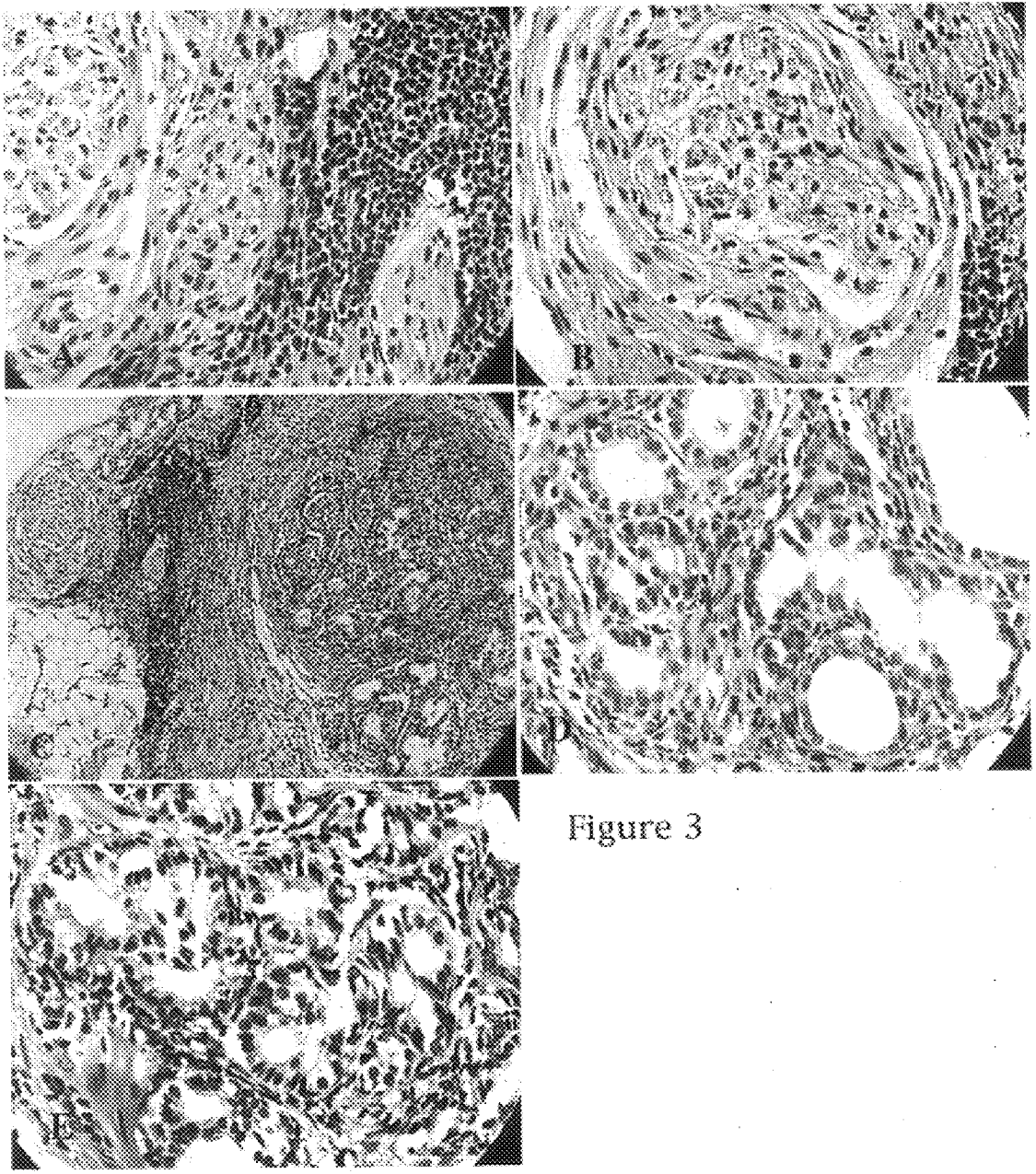
FIG. 3 shows results of staining of tissue recombinant grafts placed under the fat pad of an immunodeficient mouse.

The result of pancreatic tissue recombinant graft transplantation was assessed by morphology. Pancreatic progenitor cells have the appearance of being small and round, about 10 μm across the cell, and in a highly compacted columnar epithelium form. Acinar cells have the appearance of large clusters forming acini (FIG. 3E). Ductal cells have the appearance of small, round, about 40 μm across the cell, and a compacted, cuboidal columnar epithelium (FIG. 3D). Islet cells have the appearance of epithelial islands surrounded by acinar exocrine units (FIG. 3A, 3B, 3C, and FIG. 7).

Example 3

Figure 4:
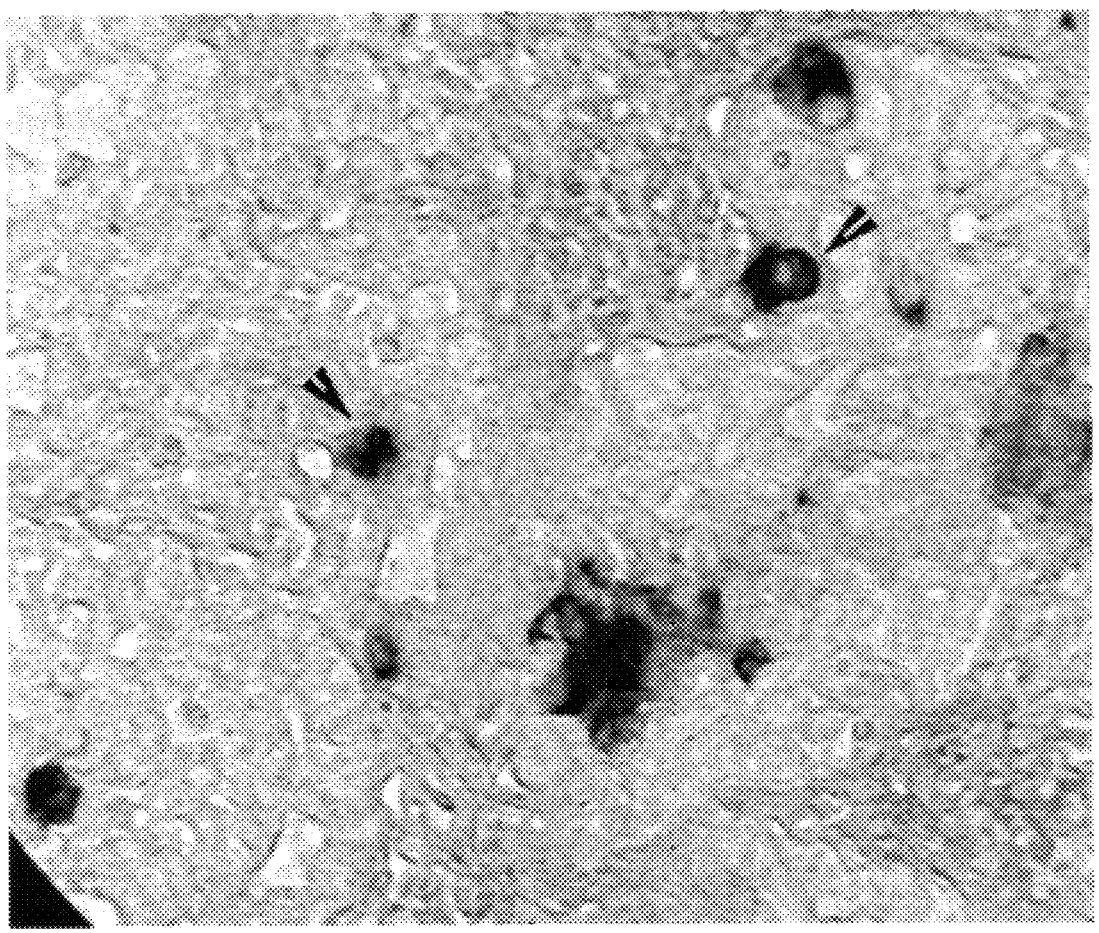
FIG. 4 shows the results of staining for glucagon (blue) and insulin (brown) in the tissue recombinant graft which was placed under the kidney capsule of an immunodeficient mouse.
Figure 5:
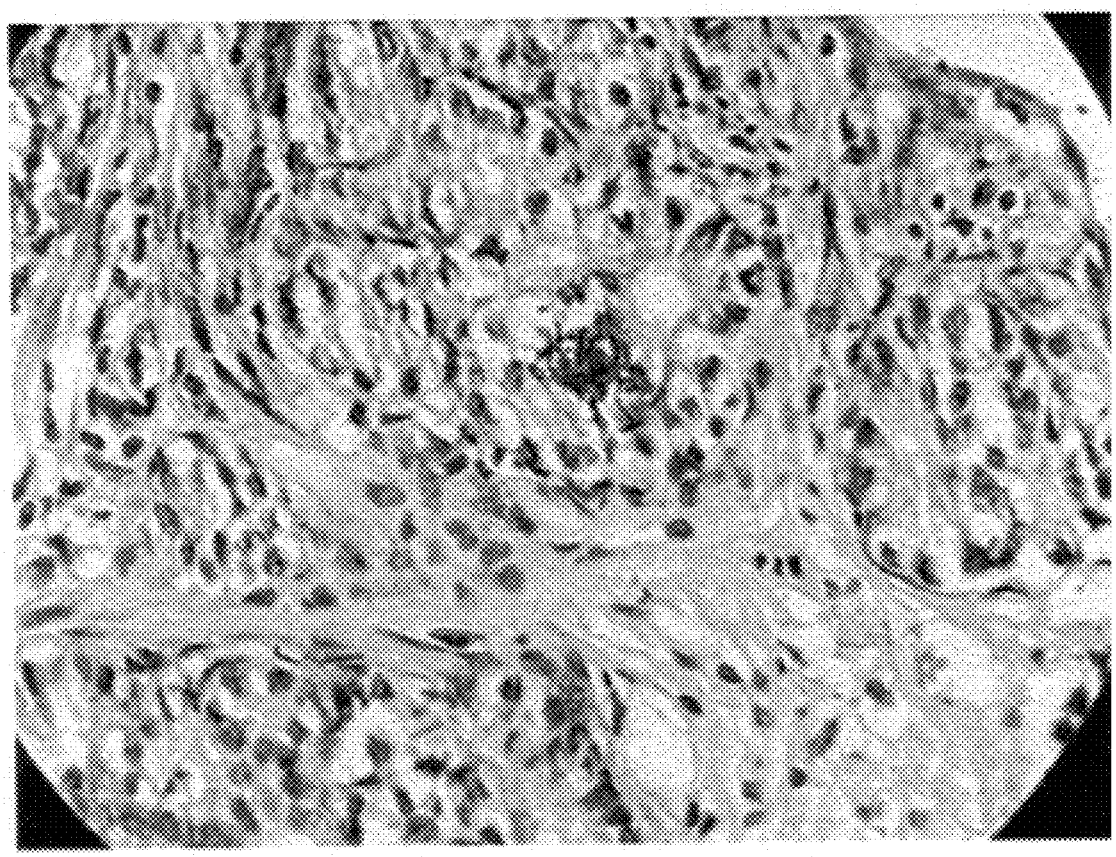
FIG. 5 shows the results of staining for insulin (brown) in the tissue recombinant graft which was placed under the kidney capsule of an immunodeficient mouse.
Figure 6:
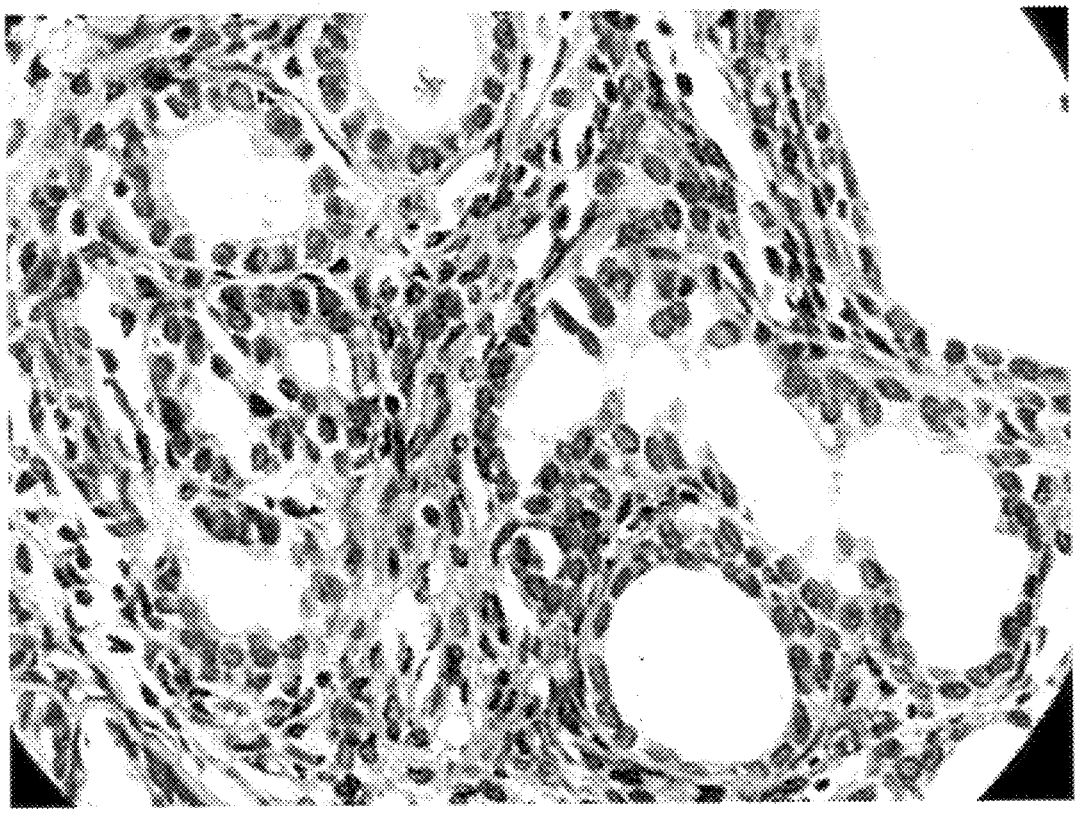
FIG. 6 shows ductal formation in the tissue recombinant which was placed under the fat pad of an immunodeficient mouse.
Figure 7:
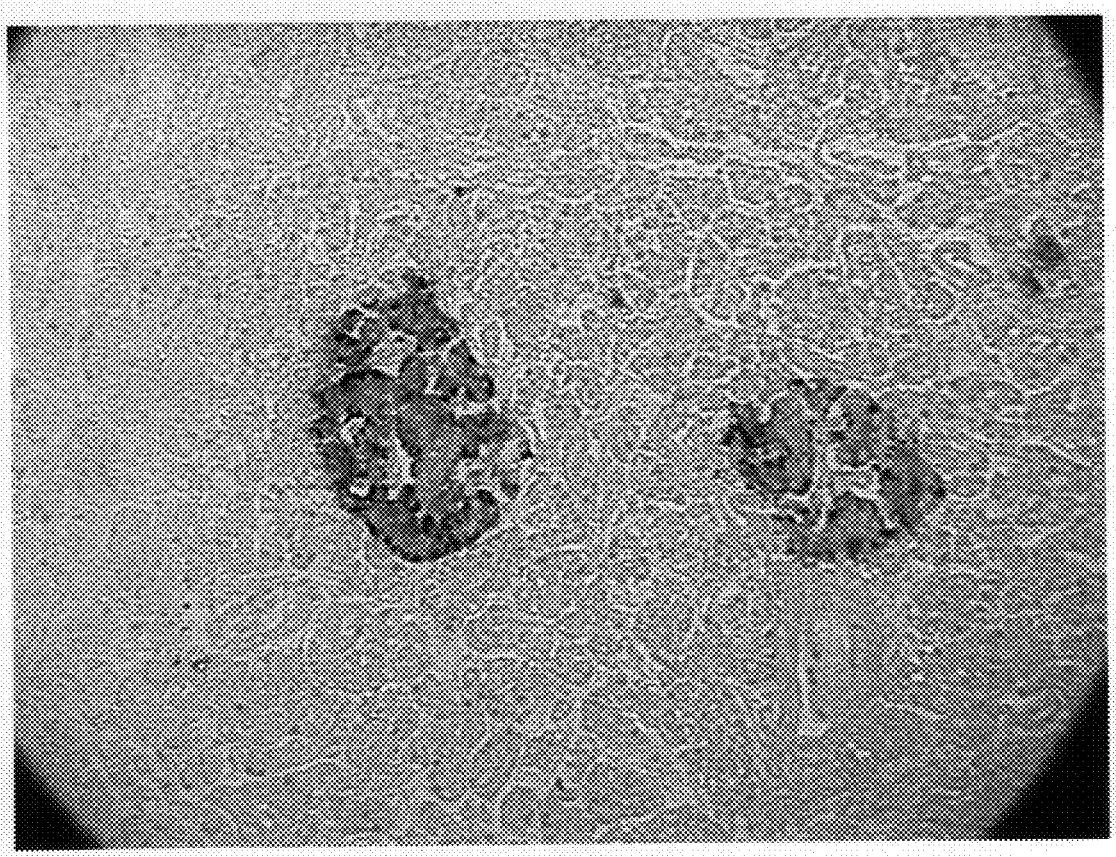
FIG. 7 shows the results of staining for glucagon (blue) and insulin (brown) in paraffin-embedded tissue section from a tissue graft which was placed under the kidney capsule of an immunodeficient mouse.

Determining the Identity of Transplanted Pancreatic Progenitor Graft Cells, Differentiation State of Pancreatic Progenitor Cells, and their Function After the pancreatic spheres have been transplanted under the kidney capsule or fat pad of mice and allowed to remain at that location for 6–8 weeks, the grafts were harvested and analyzed for identity of pancreatic cells by immunohistochemistry and function. The grafts have been shown to express insulin and glucagon (FIGS. 4, 5, and 7). Furthermore, the tissue graft recombinants have shown the formation of ductal structures (FIG. 6). Therefore, the tissue recombinant grafts yielded functional pancreatic cells that could express insulin and glucagon and form ductal structures.

What is claimed is:

1. A substantially pure population of human pancreatic progenitor cells, wherein said population of pancreatic progenitor cells will differentiate into acinar, ductal, and islet cells.

2. The population of pancreatic progenitor cells according to claim 1, wherein the pancreatic progenitor cells are isolated and maintained in serum-free media.

3. The population of pancreatic progenitor cells according to claim 1, wherein said pancreatic progenitor cells are identifiable by the expression of at least one cell marker.

4. The population of pancreatic progenitor cells according to claim 3, wherein said cell marker is selected from the group consisting of cytokeratin-19, carcinoembryonic antigen, carbonic anhydrase II, and cystic fibrosis transmembrane conductance regulator.

5. The population of pancreatic progenitor cells according to claim 4, wherein said pancreatic progenitor cells have the morphology of small and round, about 10 μm across the cell, and in a highly compacted columnar epithelial form.

6. The population of pancreatic progenitor cells according to claim 5, wherein said pancreatic progenitor cells can further differentiate into acinar cells expressing amylase and wherein said acinar cells have the appearance of large clusters forming acini.

7. The population of pancreatic progenitor cells according to claim 5 wherein said pancreatic progenitor cells can further differentiate into ductal cells expressing cytokeratin 19 and wherein said ductal cells have the morphology of small, round, about 40 μm across the cell, and a compacted, cuboidal columnar epithelial form.

8. The population of pancreatic progenitor cells according to claim 5 wherein said pancreatic progenitor cells can further differentiate into islet cells expressing insulin and glucagon and wherein said islet cells have the appearance of epithelial islands surrounded by acinar exocrine units.

9. A method of isolating the substantially pure population of human pancreatic progenitor cells of claim 1, comprising the steps of:

(a) microdissecting a source of human fetal pancreatic progenitor cells to yield a mixed population of pancreatic cells comprising pancreatic progenitor cells;

(b) placing the mixed population of pancreatic cells in nutrient media under culture conditions sufficient to sustain life of said pancreatic progenitor cells and wherein the nutrient media contains nutrients consisting of: insulin, transferrin, epidermal growth factor, ethanolamine, phosphoethanolamine, selenium, triiodothyronine, progesterone, hydrocortisone, forskolin, heregulin, aprotinin, and bovine pituitary extract;

(c) maintaining suitable culture conditions sufficient to allow pancreatic progenitor cells to form aggregate or monolayer formation; and (d) subculturing said aggregate or monolayer formation to effect isolation of the substantially pure population of pancreatic progenitor cells.

10. A method of providing a source of an immunogen to a heterologous recipient, comprising introducing a plurality of pancreatic progenitor cells as recited in claim 1 in an amount effective to induce an immune response in said recipient.

11. A method of generating human pancreatic tissue models in an immunodeficient or immunocompromised non-human mammalian recipient, comprising the step of administering human pancreatic progenitor cells of claim 1, which have been recombined ex vivo with mesenchymal tissue able to effect differentiation of said pancreatic progenitor cells, into said recipient at a location within said recipient able to support growth of said pancreatic progenitor cells.

12. A method of providing a source of pancreatic tissue-specific biological components in a pharmaceutical development of one or more drugs comprising isolating the population of human pancreatic progenitor cells as recited in claim 1, and using said pancreatic progenitor cells or any cellular part of the cells thereof as targets of one or more drugs under development.

13. A method of providing a source of nucleic acids or proteins in a development of bioassays comprising isolating nucleic acids or proteins from the human pancreatic progenitor cells as recited in claim 1 and using said nucleic acids or proteins as one or more of the principle component in the bioassays.

* * * * *